United States Patent [19]

Suzuki et al.

[11] Patent Number: 4,992,125
[45] Date of Patent: Feb. 12, 1991

[54] METHOD FOR ATTACHING ELASTIC MEMBER IN DISPOSABLE DIAPER

[75] Inventors: Migaku Suzuki; Mitsuzo Ochi; Hironori Nomura; Takamitsu Igaue; Takeshi Kudo, all of Ehime, Japan

[73] Assignee: Uni-Charm Corporation, Ehime, Japan

[21] Appl. No.: 191,371

[22] Filed: May 9, 1988

Related U.S. Application Data

[63] Continuation of Ser. No. 82,129, Aug. 6, 1987, abandoned, which is a continuation of Ser. No. 482,413, Apr. 6, 1983, abandoned.

[30] Foreign Application Priority Data

Apr. 7, 1982 [JP] Japan .................................. 57-57633

[51] Int. Cl.$^5$ ............................................. B32B 31/08
[52] U.S. Cl. .................................... 156/164; 156/229; 156/256; 156/494; 156/495; 156/519; 156/520

[58] Field of Search ............... 156/164, 229, 494, 495, 156/519, 520, 256

[56] References Cited

U.S. PATENT DOCUMENTS

| | | | |
|---|---|---|---|
| 4,081,301 | 3/1978 | Buell | 156/164 |
| 4,096,020 | 6/1978 | Basu et al. | 156/519 |
| 4,227,952 | 10/1980 | Sabee | 156/164 |
| 4,360,398 | 11/1982 | Sabee | 156/164 |
| 4,464,217 | 8/1984 | Dickover et al. | 156/164 |

*Primary Examiner*—Michael W. Ball
*Assistant Examiner*—Jeff H. Aftergut
*Attorney, Agent, or Firm*—Fred Philpitt

[57] ABSTRACT

This disclosure is directed to an apparatus adapted to cut an elastic member for fitness of opposite side edges around the user's legs into desired lengths and then to successively attach these lengths of the elastic member onto a disposable diaper.

4 Claims, 3 Drawing Sheets

4,992,125

METHOD FOR ATTACHING ELASTIC MEMBER IN DISPOSABLE DIAPER

RELATED APPLICATION

This application is a continuation of application Ser. No. 082,129 filed Aug. 6, 1987 (now abandoned), which in turn is a continuation of Ser. No. 482,413 filed Apr. 6, 1983 (now abandoned) and the benefits of 35 USC 120 are claimed relative to these prior applications.

BACKGROUND OF THE INVENTION

The present invention relates to an apparatus for attaching an elastic member to a disposable diaper and, more particularly, to an apparatus adapted to cut the elastic member for fitness of opposite side edges around the user's legs into desired lengths and then to successively attach these lengths of the elastic member onto a continuous diaper web.

In the conventional disposable diaper of so-called drawers type, the elastic member of rubber are attached to the opposite side edges of the diaper to achieve a good fitness of these side edges around the user's legs as already disclosed in U.S. Pat. No. 3,860,003. As the means for attaching such elastic member, so-called snapback method is well known and disclosed, for example, in U.S. Pat. No. 4,081,301. According to this snapback method, adhesive is applied onto a continuous elastic member longitudinally at regular intervals, this continuous elastic member is affixed with interposition of layer of thus applied adhesive onto inner surface(s) of a substantially non-elastic continuous diaper web, i.e., a backsheet and/or a topsheet, then the continuous diaper web is severed at adhesive-free portions of said elastic member into individual diapers and simultaneously said adhesive-free portions in the individual diapers are retracted from the severed ends of the respective diapers under a contractibility of these adhesive-free portions.

When this snapback method is adopted, the severed ends of the individual diaper must be provided with portions left open, through which the severed ends of the adhesive-free elastic member portions can be retracted into the individual diaper under the contractibility of the elastic member itself. Thus, the conventional disposable diaper manufactured according to this snapback method has often been susceptible to leakage of urea through such open portions of the side edges.

Also when this snapback method is adopted, the elastic member is maintained stretched and attached by adhesive applied thereon longitudinally at regular intervals onto the continuous diaper web which is also maintained under a predetermined tension during moved through steps of manufacturing. During this movement, the elastic member may sometimes partially deviate transversely of the continuous diaper web under an external force before the adhesive has not been adequately hardened. In such a case, the above-mentioned partial deviation may affect the rest of the elastic member since the latter is continuous. This may prevent the adhesive from properly functioning and, after the continuous diaper web has been severed into the individual diapers, the portions of the elastic member which should be affixed onto the diaper web may be peeled off therefrom during handling and use of the individual diapers.

A principal object of the present invention is to provide an apparatus for attaching an elastic member in a disposable diaper adapted to overcome the drawbacks encountered by the apparatus or the method of prior art.

Other objects will be apparent from the following description of preferred embodiments of the present invention.

SUMMARY OF THE INVENTION

To achieve the object as set forth above, the present invention provides an apparatus for intermittently attaching an elastic member onto a travelling continuous diaper web substantially having no elasticity, said apparatus comprising a suction roller having a peripheral surface defined by at least one protruding segment having a circumferential length corresponding to a length of each effective portion of the elastic member over which the elastic member of tape type elastically acts on the continuous web and at least one retracted segment each having a circumferential length corresponding to a length of each non-effective portion of the elastic member and having a suction zone in which said elastic member is held on said peripheral surface in a stretched state; a cutter located in opposition to the peripheral surface of said suction roller and adapted to cut the non-effective portions of said elastic member in said retracted segment; and a nip roller located in opposition to the peripheral surface of said suction roller adjacent an end of said suction zone at which the elastic member is relieved of the suction and adapted to press said elastic member which has been cut by said cutter into a given length and applied with adhesive against said continuous web so as to affix said elastic member onto said continuous web with interposition of said adhesive.

PREFERRED EMBODIMENTS OF THE INVENTION

Figure 1:
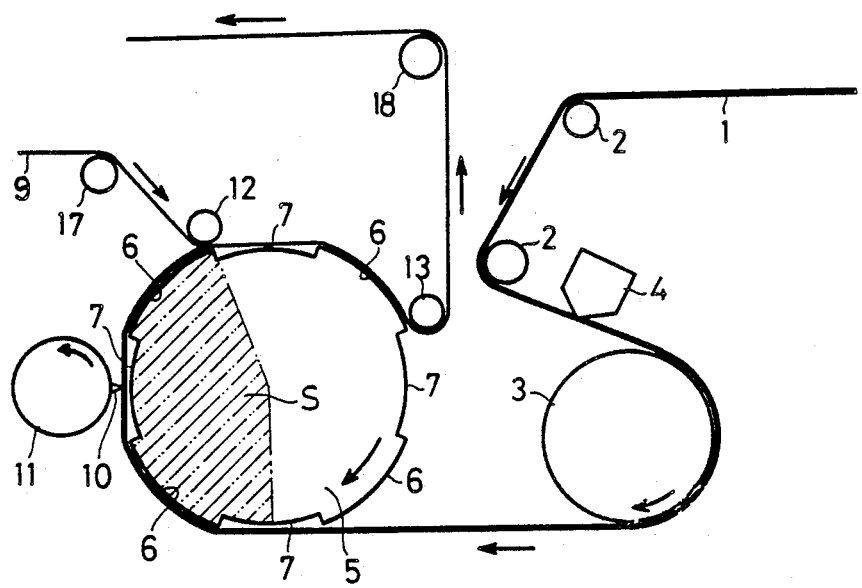
FIG. 1 is a simplified sectional side elevation view showing an important part of the apparatus constructed in one of possible manners of execution according to the present invention.

FIG. 1 schematically illustrates an important part of the apparatus according to the present invention. Elastic member 1 as a continuous tape of rubber, urethane foam or the like is continuously fed at a constant velocity from its feeding mechanism (not shown) via guide rollers 2 to a holding roller 3. Immediately before the holding roller 3, there is arranged in the path of the elastic member 1 means 4 for application of adhesive of hot melt type realized, for example, as a nozzle adapted to apply said adhesive longitudinally on one side of said member 1 over predetermined lengths at regular intervals The holding roller 3 is so arranged that the elastic member 1 may be fed forward therefrom without any slippage of the elastic member 1 on its peripheral surface, and a circumferential velocity of this holding roller 3 is adjustable to an intermediate value of a feed velocity of said member 1 and a circumferential velocity of a suction roller 5 as will be described later.

Figure 2:
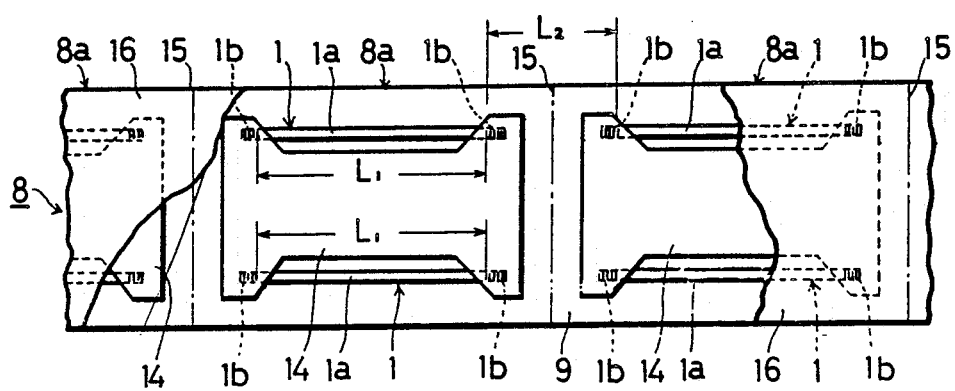
FIG. 2 is a plan view showing a continuous diaper web as partially broken away.

The elastic member 1 which has left the holding roller 3 is now guided onto the suction roller 5. The suction roller 5 contains therein a suction device (not shown) arranged at a fixed position to provide a suction zone S and has a peripheral surface rotating through said suction zone S. This peripheral surface is of a meshy structure so that a desired effect of suction may be achieved in said suction zone S through this peripheral surface of meshy structure, and defined by protruding segments 6 and retracted segments 7, which are alternately arranged. A circumferential length of each protruding segment 6 corresponds to a length $L_1$ of each adhesive coated area $1a$ along which the elastic member 1 acts on a substantially non-elastic web or backsheet 9 forming a continuous diaper web 8 as will be described in reference with FIG. 2 while a circumferential length of each retracted segment 7 corresponds to a length $L_2$ of each adhesive-free area $1b$ along which the elastic member 1 has no elastic effect upon the backsheet 9 (said adhesive-free area $1b$ has been cut and shrunk in the condition as shown by FIG. 2).

Around the suction roller 5, there is provided a cutter roller 11 including a knife-edge 10 in opposition to said suction roller 5. A circumferential velocity as well as cutting operation of the cutter roller 11 are synchronized with a circumferential velocity of the suction roller 5 so that the knife-edge 10 rotating together with the cutter roller 11 comes to the middle of each retracted segment 7.

The backsheet 9 is transported via a guide roller 17 to the suction roller 5, then guided by a first nip roller 12 arranged close to the peripheral surface of said suction roller 5 at one end of the suction zone S and a second nip roller 13 also arranged close to the peripheral surface of said suction roller 5 at a suitable distance from said first nip roller 12 along a portion of said peripheral surface of said suction roller 5.

The apparatus according to the present invention operates with the respective mechanisms, the elastic member 1 and the backsheet 9 which are respectively arranged as mentioned above. It will be seen from FIG. 1 that the elastic member 1 is longitudinally applied by the applicator means 4 with adhesive of hot melt type (not shown) on one side of said elastic member 1 at regular intervals before said elastic member 1 reaches the holding roller 3 and further transported from this holding roller 3 onto the suction roller 5 in close contact with the peripheral surface thereof. The suction roller 5 has its circumferential velocity higher than the circumferential velocity of the holding roller 3 so that the elastic member 1 may be longitudinally stretched by a length depending on such difference of the circumferential velocities. Here is also provided an arrangement such that each adhesive-coated area $1a$ (having the length $L_1$) of the elastic member 1 may be exactly placed on the associated one of the protruding segments 6 of the suction roller 5 while each adhesive-free area $1b$ (having the length $L_2$) may be exactly placed on the associated one of the retracted segments 7 of said suction roller 5, as the portion of the peripheral surface of said suction roller 5 enters the suction zone S. Although not shown, a belt may be provided to maintain the backsheet 9 in close contact with the elastic member 1 along the peripheral surface of the suction roller 5 extending between the first nip roller 12 and the second nip roller 13, if necessary.

Figure 3:
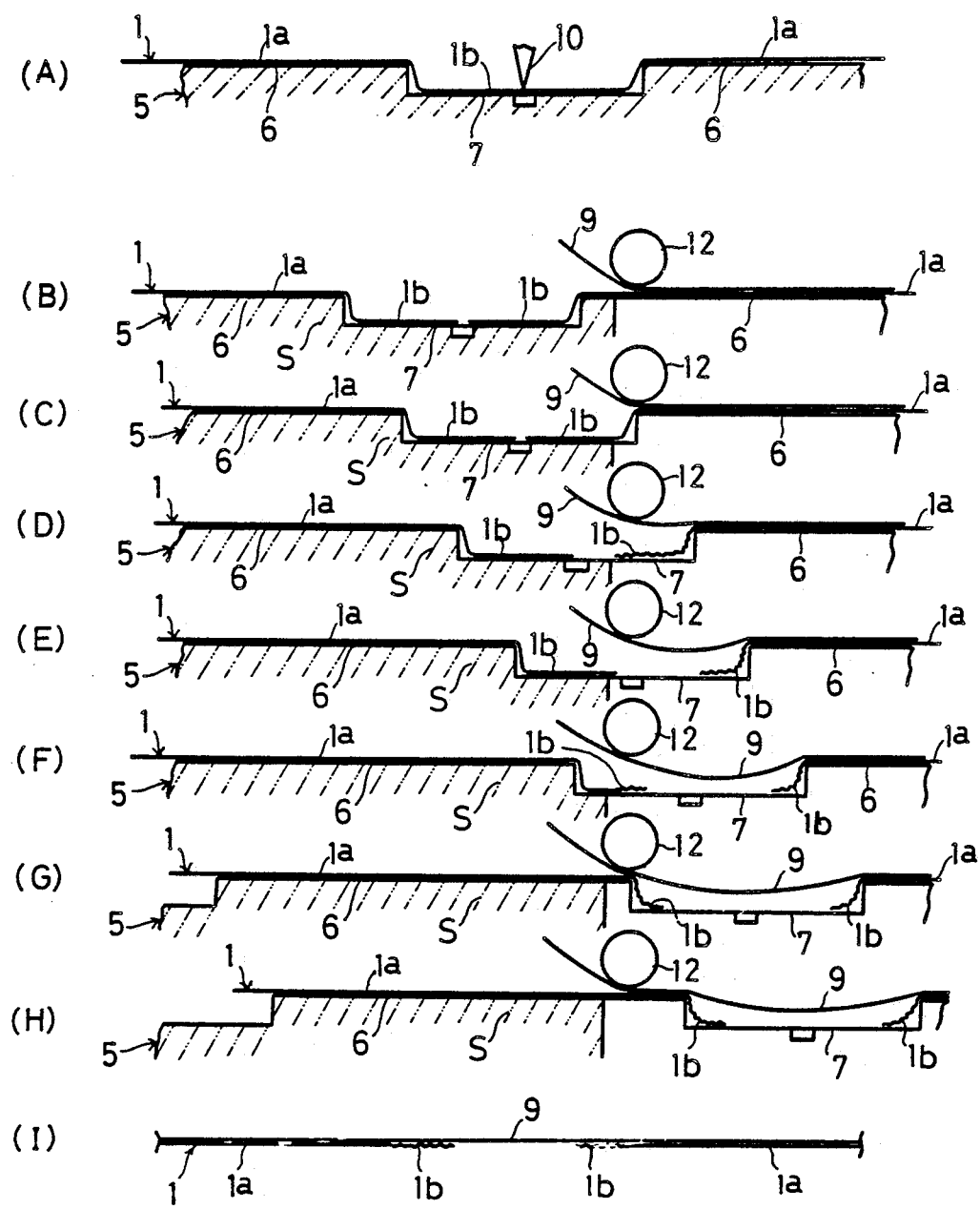
FIG. 3 is a schema illustrating the important part of the apparatus according to the present invention in developed views in association with respective steps in which material to be treated is successively treated.

The manner in which the apparatus according to the present invention further operates from the state as mentioned above will be now considered in reference with FIG. 3 schematically showing the important part of the apparatus according to the present invention in developed views in association with respective steps in which material to be treated is successively treated.

In a state as illustrated by FIG. 3(A), the knife-edge 10 mounted on the cutter roller 11 is positioned at the middle of the retracted segment 7 of the suction roller 5 and cuts the adhesive free area $1b$ of the elastic member 1 lying on this retracted segment 7. Said retracted segment 7 remains within the suction zone S during this cutting operation and, therefore, the adhesive-free area $1b$ of the elastic member 1 remain sucked against the peripheral surface of the suction roller 5 even after said cutting.

This effect of suction is maintained until a state of FIG. 3(B) is reached, in which the suction roller 5 is further rotated and said retracted segment 7 attains the end of the suction zone S. Before the state of FIG. 3(B) is reached, the portion of the elastic member 1 which has been released from the effect of suction has already been applied by the first nip roller 12 onto the backsheet 9.

As the suction roller 5 is further rotated and accordingly the retracted segment 7 approaches the end of the suction zone S, the elastic member 1 is relieved of the effect of suction progressively from its portion being applied onto the backsheet 9 (see FIG. 3(C)) and, when a contractibility of said elastic member 1 overcomes the effect of suction tending to hold said elastic member 1 immediately before the cut end of said adhesive-free portion $1b$ leaves the end of said suction zone S, said cut end of said adhesive-free portion $1b$ is released from a holding effect and said adhesive free portion $1b$ begins to be shrunk from said cut end (see FIG. 3(D) and FIG. 3(E)).

Such shrinkage of the adhesive-free area $1b$ of the elastic member 1 is repeated in the subsequent adhesive-free areas $1b$ in the same manner as above-mentioned, i.e., such shrinkage occurs as the respective adhesive-free areas $1b$ leave the suction zone S (see FIG. 3(F)).

When a further rotation of the suction roller 5 moves the retracted segment 7 until its rear end passes beyond the end of the suction zone S, the elastic member 1 immediately after relieved of the suction is applied under a pressure of the first nip roller 12 onto the backsheet 9 (see FIG. 3(G)). Thereafter, the elastic member 1 is successively applied onto the backsheet (see FIG. 3(H)) and, as a result, the elastic member 1 is applied onto the backsheet 9 longitudinally at regular intervals with the adhesive-free areas $1b$ shrunk (see FIG. 3(I)). These diaper components thus treated are fed via the second nip roller 13 and a guide roller 18 to a subsequent stage of assembly (not shown).

FIG. 2 illustrates construction of the continuous diaper web. The continuous diaper web 8 comprises the backsheet 9 formed by material such as polyethylene film, the elastic member 1 which has been cut and applied by adhesive previously coated thereon onto said backsheet 9 longitudinally at regular intervals, absorbent bodies 14 made of fluffy pulp or the like and fixed to the respective pieces of the elastic member 1, and a topsheet 15 dimensionally identical to said backsheet 9 and made of nonwoven fabric or the like joined to these members. The continuous diaper web comprising these members is completely assembled at the stage of assembly (not shown) and then severed along lines 15 between respective pairs of adjacent absorbent bodies 14 into individual diapers 8a. The respective absorbent bodies 14 and the topsheet 16 are joined by adhesive of hot melt type to the rest members, i.e., the backsheet 9 and the elastic member 1 after the pieces of this elastic member 1 have been applied to said backsheet 9. It is obvious that the backsheet 9 and the topsheet 15 in the individual diaper 8a should be joined also along their peripheries.

With the apparatus according to the present invention, the leading end of the elastic member 1 to be applied to the backsheet 9 in the state of FIG. 3(G) is applied by the first nip roller 12 onto said backsheet 9 immediately after relieved of the sucking action of the suction roller 5 in the suction zone S. It is preferred to make the time elapsing from said relief of the sucking effect to the actual application of the elastic member 1 onto the backsheet 9 as short as possible, because said leading end of said elastic member 1 might be shrunk depending on the length of said elapsing time. As an effective measure to this, the circumferential velocity of the suction roller 5 may be set to a relatively high level, the first nip roller 12 may be placed, as closely as possible, adjacent the end of the suction zone S of said suction roller 5, and the working portions or the retracted segments 7 of said suction roller 5 may be provided along their edges with an adequately high sucking action, with a remarkable success.

It will be apparent from the aforegoing description of the embodiments that, with the apparatus according to the present invention, the continuous elastic member 1 has previously been cut into given lengths and successively applied onto the backsheet longitudinally at regular intervals already during formation of the continuous diaper web and the individual diapers 8a free from all the drawbacks of the conventional diapers manufactured according to so-called snapback process can be obtained at a high efficiency.

The applicator means 4 for application of adhesive onto the elastic member 1 is located between a supply source of this member 1 and the holding roller 3 and the circumferential velocity of said roller 3 is adjusted to an intermediate value of the feed velocity of said member 1 itself and the circumferential velocity of the suction roller 5 so that a percentage of elongation of said member 1 at a portion coming in contact with said means 4 may be selectively adjusted from zero to a desired percentage of elongation. With respect to, for example, said member 1 of material which is apt to be thermally affected by adhesive of hot melt type applied from said means 4, such application of adhesive may be carried out at said percentage of elongation adjusted to a relatively low value. However, it should be understood here that, although not shown, the applicator means 4 is possible to be located between the holding roller 3 and the suction roller 5 so that the elastic member 1 may be applied with adhesive, and on the contrary, between the first nip roller 12 and the guide roller 17 so that the backsheet 9 may be applied with the adhesive.

The apparatus according to the present invention has been described and illustrated with respect to the case in which the adhesive of hot melt type is applied onto the elastic member 1 longitudinally at regular intervals. However, it should be clear that, even when there is provided a suitable measure adapted for intermittently stopping the dispensing of adhesive from the applicator means 4 to achieve such manner of application, the adhesive may often be applied beyond the borders of the adhesive coated area 1a onto the adjacent adhesive-free areas 1b of the elastic member 1. If the adhesive is applied onto the adhesive-free areas 1b of the elastic member 1 and these adhesive-free areas 1b are joined to the backsheet 9 while said adhesive-free areas 1b remain stretched, the contractibility of said adhesive-free areas 1b would deform the individual diapers 8a and prevent good fitness of these diapers around the user's body, since these adhesive-free areas 1b will occupy the waist line in the individual diaper 8a. With the apparatus according to the present invention, however, such a problem can be effectively avoided even if the adhesive is applied beyond the borders of the adhesive-coated areas 1a onto the adhesive-free areas 1b, said adhesive-free areas 1b are applied in the retracted segments 7 onto the backsheet 9 in the shrunk state.

Figure 4:
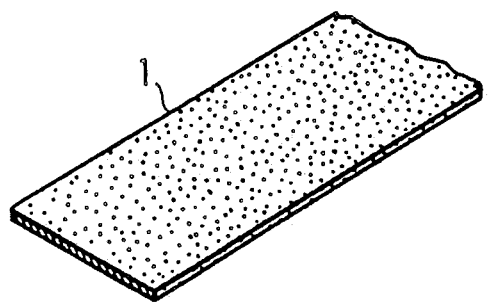
FIG. 4 is a fragmentary perspective view showing an embodiment of elastic member used in the apparatus according to the present invention.
Figure 5:
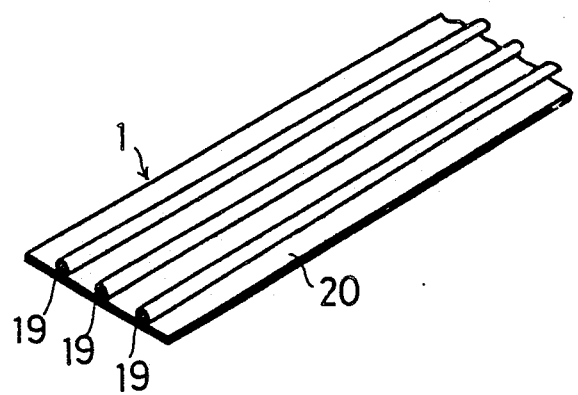
FIG. 5 is a view similar to FIG. 4 but showing another embodiment of elastic member used in the apparatus according to the present invention.

A preferred embodiment of the elastic member 1 used in the apparatus according to the present invention is illustrated by FIG. 4. This specific embodiment is in the form of polyurethane tape having a width of 5 to 40 mm, a thickness of 0.5 to 2 mm and a tensile stress of 100 to 300 g. As an embodiment of the present invention, the inventors stretched 100 mm of polyurethane tape having an initial thickness of 1.5 mm to 225 mm, applied two lines of adhesive of hot melt type commercially available under the trade name "KANEBO NSC" which is rubber-based and sticky at a normal temperature onto one side of said tape transversely spaced from each other, adjusted a suction pressure of the suction roller 5 to $-600$ mmAq and affixed said tape onto the backsheet 9 made of polyethylene film at a feed velocity of said tape adjusted to 100 m/min. It has been found that said tape can be stably held on the peripheral surface of the suction roller 5 under a sucking effect and affixed onto the backsheet 9 with a high stability. After stretching, the taper presented a width of 20 mm, a thickness of 1 mm and a contraction stress of 250 g. Another embodiment of the elastic member 1 used in the apparatus according to the present invention is illustrated by FIG. 5. This elastic member comprises a plurality of rubber threads 19 stretched at a predetermined percentage of elongation, applied with adhesive of hot melt type and affixed onto a tape 20 of polyethylene film or the like which is extremely thin, flexible and 10 to 40 mm wide transversely spaced from one another. When such embodiment of the elastic member 1 is adopted, the holding roller 3 is not provided but stretcher means and supply means for said tape 19 are provided so that the elastic member 1 formed as above mentioned may be fed to the suction roller 5. The applicator means 4 may be preferably a nozzle having a plurality of slots arranged transversely at regular intervals so that said slots may dispense and apply adhesive of hot melt type peripheral surfaces of said respective rubber threads and regulate the intervals at which the rubber threads are affixed onto said tape 19. Said rubber threads preferably have a cross-section of 0.03 to 0.45 mm² per each thread, a total cross-section of 0.09 to 1.35 mm², and present a tensile stress of 100 to 300 g when stretched at an elongation percentage of 100 to 400%.

What is claimed is:

1. A method for attaching portions of an elongated elastic member to a travelling continuous diaper web that has substantially no elasticity, said method comprising (a) moving an elongated elastic member along a predetermined path and supporting it in at least a portion of that path by the application of suction against the underside of said elastic member, (b) applying adhesive to spaced apart portions of the upper side of said elastic member to thereby establish a series of spaced apart adhesively coated sections separated by intermediate adhesive-free sections, (c) bringing a diaper web into contact with the upper surface of said elastic member so that the adhesively coated portions of the elastic member will be joined to said diaper web, and (d) subsequentially cutting each said adhesive-free section prior to step (c) so that upon the completion of step (c) the continuous diaper web will have attached to it a series of separated lengths of elastic member, each such length of elastic member being composed of a central adhesively coated section and opposite end sections that are not adhesively coated.

2. A method according to claim 1 wherein said elastic member is maintained in a longitudinally stretched condition at least during step (a).

3. A method according to claim 2 wherein said opposite end sections of the elastic member that are not adhesively coated return to an unstretched condition following the cutting set forth in step (d).

4. A method according to claim 1 wherein the application of suction to the undersigned of said elastic member is terminated at about the same time or shortly after the diaper web comes into contact with the upper surface of the elastic member as set forth in step (c).

* * * * *